United States Patent [19]

West

[11] 3,947,124
[45] Mar. 30, 1976

[54] ANALYTICAL SPECTROELECTROCHEMISTRY
[75] Inventor: Thomas Summers West, Croydon, England
[73] Assignee: National Research Development Corporation, London, England
[22] Filed: Oct. 18, 1974
[21] Appl. No.: 516,016

[30] Foreign Application Priority Data
Oct. 26, 1973 United Kingdom............ 50038/73
Aug. 12, 1974 United Kingdom............ 35449/74

[52] U.S. Cl. ................ 356/74; 250/458; 356/36; 356/72; 356/96
[51] Int. Cl.² .................. G01J 3/42; G01N 21/52
[58] Field of Search ............ 356/36, 74, 72, 85, 89, 356/93–97, 201, 246; 204/1 T, 195 R; 250/458, 461

[56] References Cited
OTHER PUBLICATIONS

Strojek et al., *Electroanalytical Chemistry and Interfacial Electrochemistry*, Vol. 16, Apr. 1968, pp. 471–483.
Laser et al., *Electroanalytical Chemistry and Interfacial Electrochemistry*, Vol. 35, Mar. 1972, pp. 405–414.
Gruver et al., *Electroanalytical Chemistry and Interfacial Electrochemistry*, Vol. 36, Apr. 1972, pp. 85–99.
Prostak et al., *The Journal of Physical Chemistry*, Vol. 72, No. 7, July 1968, pp. 2576–2582.
Tallant et al., *Analytical Chemistry* Vol. 41, No. 6, May 1969, pp. 835–838.

Primary Examiner—Alfred E. Smith
Assistant Examiner—F. L. Evans
Attorney, Agent, or Firm—Cushman, Darby & Cushman

[57] ABSTRACT

In a method of analytical spectrometry, material to be analysed is introduced in solution between a pair of charged electrodes so as to produce a light-absorbing atomic or molecular species by electrolysis at an electrode surface. A beam of light of an appropriate wavelength is directed through the solution into the vicinity of the relevant surface and light emerging from this vicinity is detected. Specific forms of apparatus are described for practising the method, using either absorption or fluorescence techniques.

27 Claims, 8 Drawing Figures

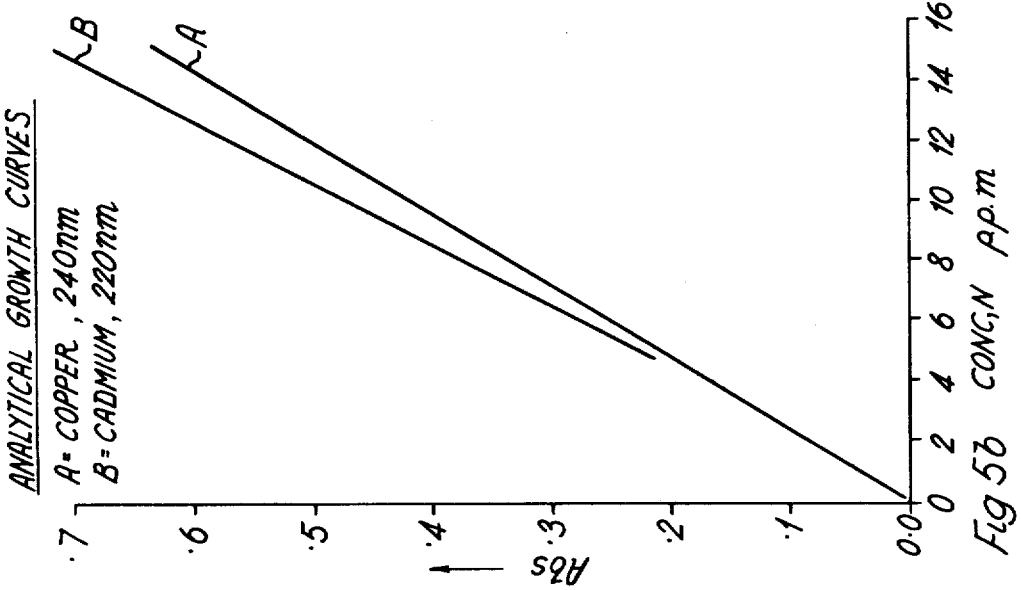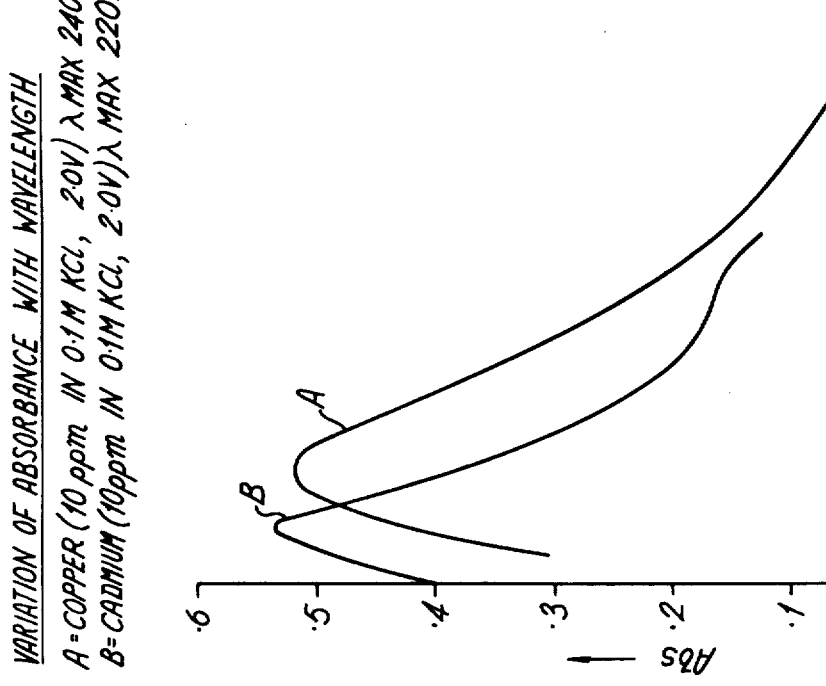

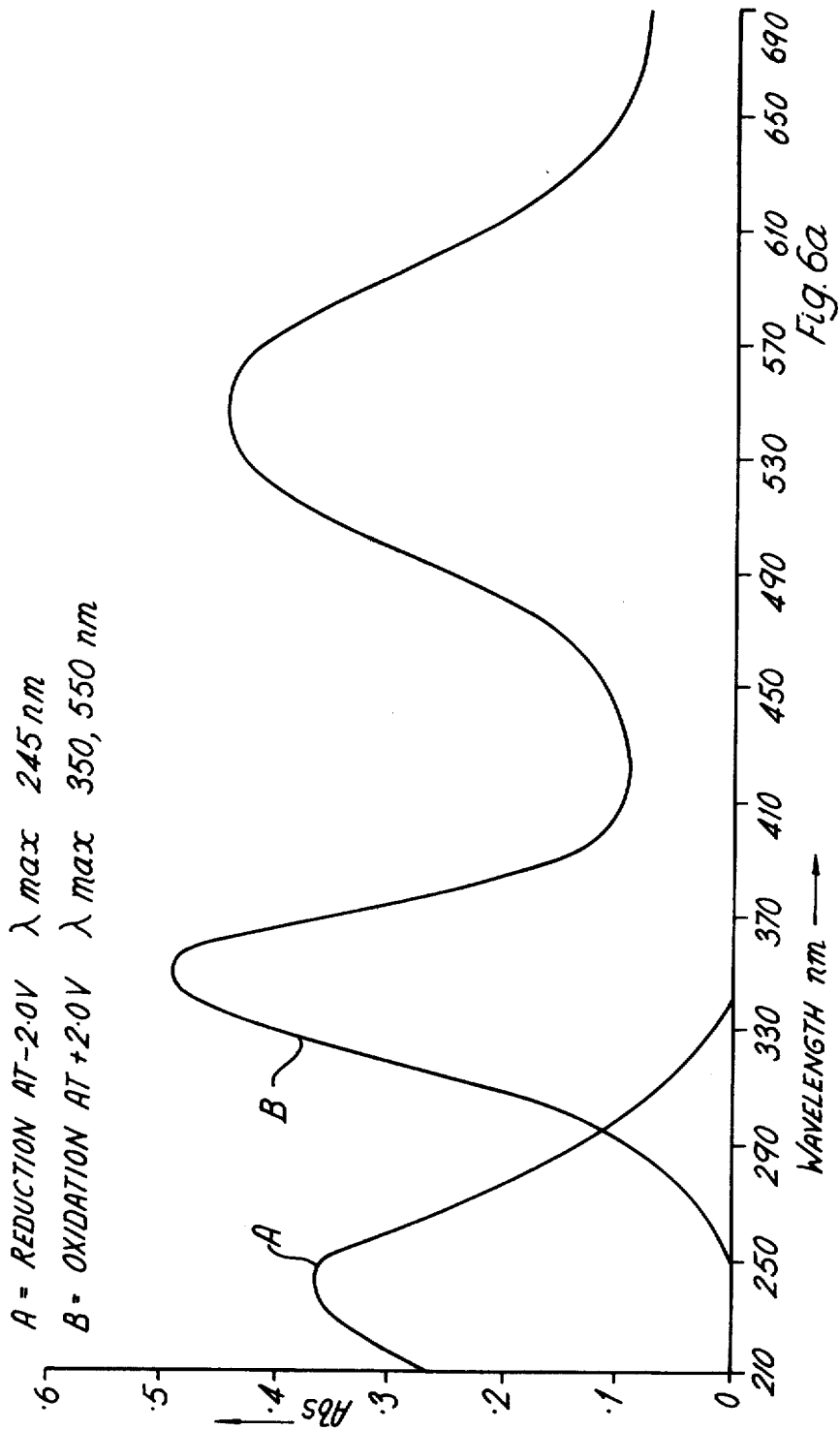

ANALYTICAL SPECTROELECTROCHEMISTRY

The present invention concerns analytical spectrometry.

One method commonly used in this field is that known as atomic absorption spectrometry, in respect of which two techniques are already well known. In the first the sample to be analysed is volatilized in a flame through which light having a wavelength characteristic of the atoms to be analysed is passed; it is to be understood that in this specification the term "light" is used in the sense of including ultra-violet and infra-red radiation as well as visible radiation. The light is subsequently detected so that any fall in intensity caused by the excitation of the vaporised atoms can be measured. In the second technique the sample to be analyzed is placed on an element or within a chamber which is heated without flame (e.g. electrically or by flash-tube heating) to volatilize the sample in the presence of a protective inert gas. A light source and detection system similar to that used with the flame technique are employed in an analogous manner. Both of these techniques have advantages and disadvantages which are well known to those skilled in the art. Similar techniques are also employed in the method known as atomic fluorescence spectrometry; in this case a cloud of free atoms is excited by light of an appropriate wavelength and the intensity of light emitted by the atoms at a different wavelength is detected.

The present invention is concerned with novel methods of spectrometry in which instead of working in the gas phase the species to be analysed are electrogenerated and examined directly in solution.

According to one aspect of the present invention there is provided a method of analytical spectrometry wherein material to be analysed is introduced in solution between a pair of charged electrodes so as to produce a light-absorbing species in solution by electrolysis at an electrode surface, the method involving directing through the solution into the vicinity of said surface a beam of light having a wavelength such as to interact with said light-absorbing species, and detecting light emerging from the vicinity of said surface.

In accordance with another aspect of the present invention, there is provided an apparatus for use in analytical spectrometry comprising a pair of electrodes in a cell, means for directing a beam of light into said cell at grazing incidence to a surface of at least one of said electrodes, and means for detecting light emerging from the vicinity of said surface.

Embodiments of the present invention will now be described by way of example and with reference to the accompanying drawings, in which.

Figure 4:
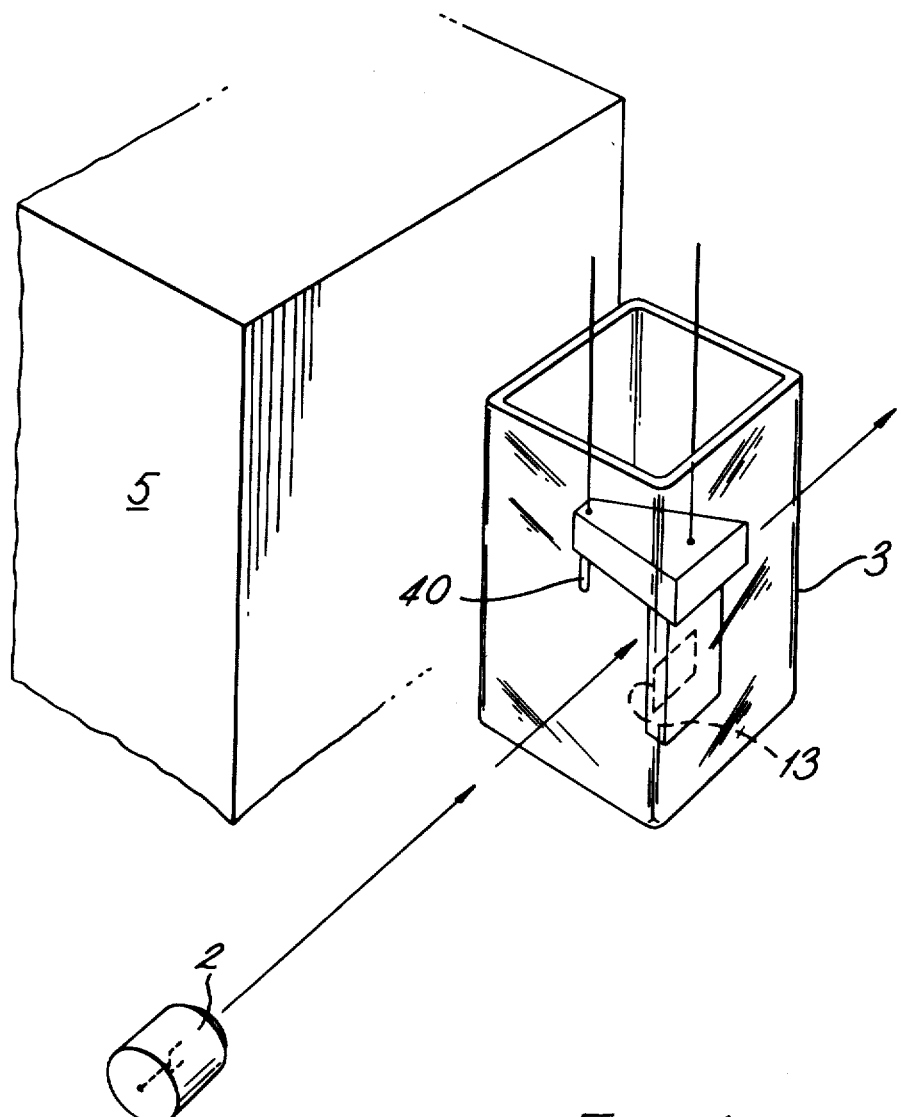

FIG. 4 is a diagrammatic perspective view of an apparatus suitable for fluorescence spectrometry; and FIGS. 5a and 5b, and 6a and 6b are graphs showing sample results for both inorganic and organic samples.

Figure 1:
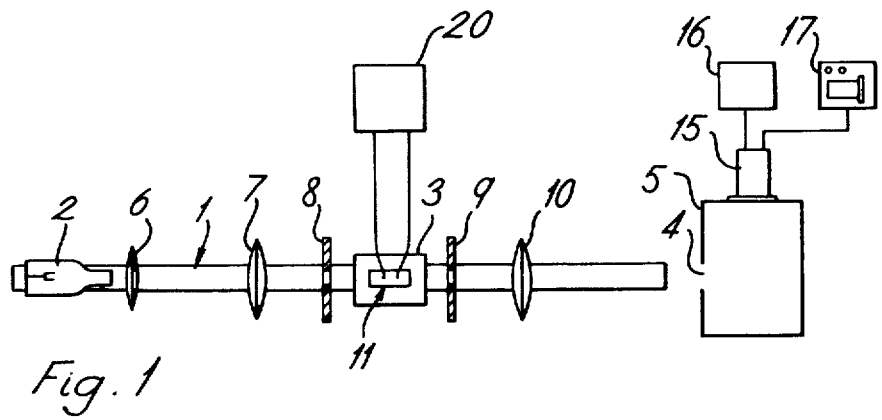
FIG. 1 is a diagrammatic representation of an absorption spectrometer, with certain components shown as in a plan view.
Figure 2:
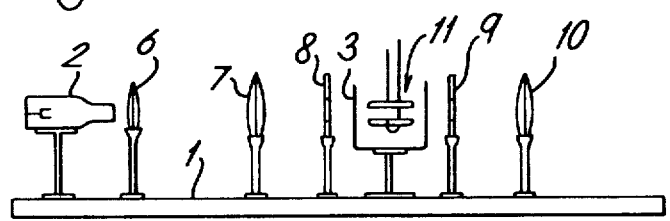
FIG. 2 is a diagrammatic elevation of the optical bench of the spectrometer of FIG. 1.

The absorption spectrometer shown in FIGS. 1 and 2 comprises an optical bench 1 on which are mounted various components including a lamp 2 (which may suitably be of the hollow cathode type) arranged to direct a narrow beam of light through a transparent cell 3 to the entrance slit 4 of a monochromator 5; the internal details of the monochromator 5 are of conventional form and are therefore not shown in the drawing. Accurate collimation of the beam is provided by lenses 6 and 7 and a pair of slits formed in plates 8 and 9 mounted one on each side of the cell 3, and the beam is concentrated on the slit 4 by means of a further lens 10. Within the cell 3 is an electrode system 11, shown in greater detail in FIG. 3, which comprises a pair of platinum plates 12 and 13 disposed horizontally so as to face each other; the spacing between the electrodes 12 and 13 is not in any way critical, but may suitably have a value of about five millimeters. Parts of the electrodes 12 and 13 are protected by a suitable substance 14 so that only the lower face of the upper electrode 12 and the upper face of the lower electrode 13 are exposed. For example the substance 14 could be paraffin wax or the electrodes could be set in a thermoplastic material. The collimated beam of light, which may typically have a diameter of 0.5 millimeter, is arranged to pass through the space between the electrodes 12 and 13 at grazing incidence to the upper face of the lower electrode 13. The term "grazing incidence" as used in this specification is intended to cover the cases where the beam of light is either partially obscured by the surface of the electrode or the optical axis of the beam is not further than one millimeter from the surface of the electrode. The light dispersed by the monochromator 5 falls on a photomultiplier tube 15 energised by a power supply 16 and an output signal from the tube 15 is fed to a chart recorder 17. Naturally other forms of output display could be used if desired. The electrodes 12 and 13 are connected to a function generator 20 so that the potential difference between them can be varied as desired.

In use of the apparatus material to be analysed is dissolved and then added to a quantity of an electrolyte solution taken from a bulk supply which may be kept under nitrogen and continuously de-aerated, the mixture being transferred to the cell 3 in an amount sufficient to cover the electrode system 11; suitable electrolytes are for example aqueous solutions of potassium chloride at a concentration of 0.1M and potassium sulphate at a concentration 0.03M. The solution in the cell 3 is further de-aerated by introducing nitrogen via an inlet tube 21, the nitrogen leaving via an outlet tube 22. With the apparatus adjusted so that the recorder 17 initially registers zero absorbance, the recorder 17 is started and the function generator 20 is operated so as to apply to the electrode system 11 a voltage step function which steps the voltage between the electrodes 12 and 13 from zero to a preset required value, the polarity of the voltage of course depending on whether the electrode 13 (at whose exposed surface light-absorbing species are generated) is required to operate as a cathode or as an anode. As a result, there is a transient increase in the absorbance registered by the recorder 17, and the voltage between the electrodes 12 and 13 is maintained at the preset value until a maximum value of absorbance is reached. The recorder 17 is then stopped and the voltage switched back to zero. The preset value of the voltage typically has a magnitude in the range of about one to two volts, a practical upper limit being imposed by the onset of evolution of gas bubbles in the electrolyte.

After a measurement is taken it is essential that the working electrode 13 be thoroughly cleaned so as to prevent it being contaminated. The cleaning technique may vary but typically the sample solution is sucked out of the cell 3, for example by means of a glass capillary 23, and a relatively high positive voltage (up to 5 volts) is applied to the electrode 13, while washing through with dilute potassium chloride solution, so that the electrode 13 is cleaned by anodic stripping. If necessary any surface oxide formed may be reduced by reversing the polarity of the voltage. The electrodes 12 and 13 are finally washed with water before the next sample is placed in the cell 3.

When carrying out analyses for metals, the electrode 13 is operated as a cathode, and the electrolytic mechanism by which the absorbing species are produced at the cathode surface is thought to involve electrons tunnelling from the cathode surface. The electrons may react directly with the hydrated cations of the sample solution to produce reduced species which are likely to be hydrated free atoms. Alternatively the electrons may become hydrated and pass into the solution where they similarly reduce the hydrated cations at macroscopic distances from the cathode surface. Each reduced species exhibits absorption phenomena at a characteristic reduction potential and exhibits a characteristic absorption spectrum which frequently has half-spectral bandwidth in the region of 10 – 100 nanometers provided that the beam of light used to produce the absorption spectrum passes with grazing incidence along the cathode surface.

The spectra of these atoms generated in a condensed phase (as opposed to the gas phase technique of all other forms of atomic spectrometry) are different from those of the conventional techniques due to pressure broadening and the presence of liganding species such as the solvent etc.

Figure 3:
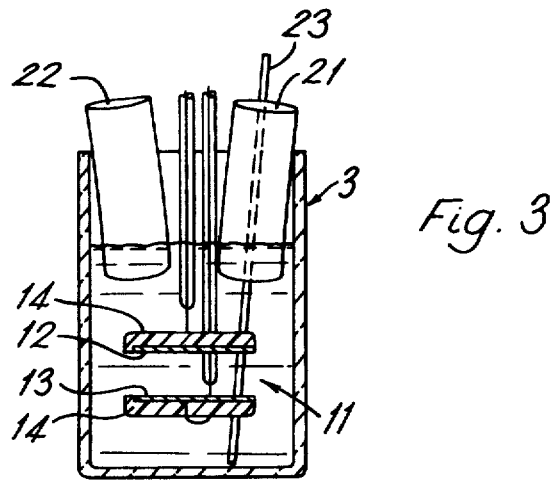
FIG. 3 is a detailed view of the sample cell of the spectrometer of FIG. 1.

The results obtained with metals when using the apparatus shown in FIGS. 1 to 3 may be illustrated by considering the cases of copper and cadmium. In FIG. 5a the curves A and B respectively show the variations of absorbance with wavelength (expressed in nanometers) for these two metals, in both cases at a concentration of 10 p.p.m. using a background electrolyte of 0.1M potassium chloride and a voltage of 2 volts. Under the same conditions, the variations of absorbance with concentration (expressed in p.p.m.) for copper and cadmium, respectively at wavelengths of 240 and 220 nm, are shown respectively by the curves A and B of FIG. 5b. Similar results have also been obtained for example for the metals iron, lead, zinc, cobalt, nickel and manganese.

Simple variation of the technique described above should allow the atoms to be generated in conducting glasses formed by freezing of the solution to low temperatures by liquid nitrogen or the like.

In a modified method according to the invention, a metallic specimen may be analysed by making it the anode and anodically stripping material from it into solution, the atoms being examined spectroscopically either as they are electrogenerated at the anode surface or in the manner previously described at a cathode surface. In an extension of this technique material to be analysed which is available only in very dilute solution may be initially concentrated by electrodeposition on a suitable substrate, which is then used as an anode from which the deposit is anodically stripped during the spectroscopic examination.

Although the description so far has concentrated on the analysis of inorganic atoms the invention is also applicable to molecular analysis of organic compounds and this is potentially applicable in the analysis of drugs, carcinogens and the like where spectroscopically different species may be formed by reduction or oxidation at electrode surfaces.

Figure 6B:
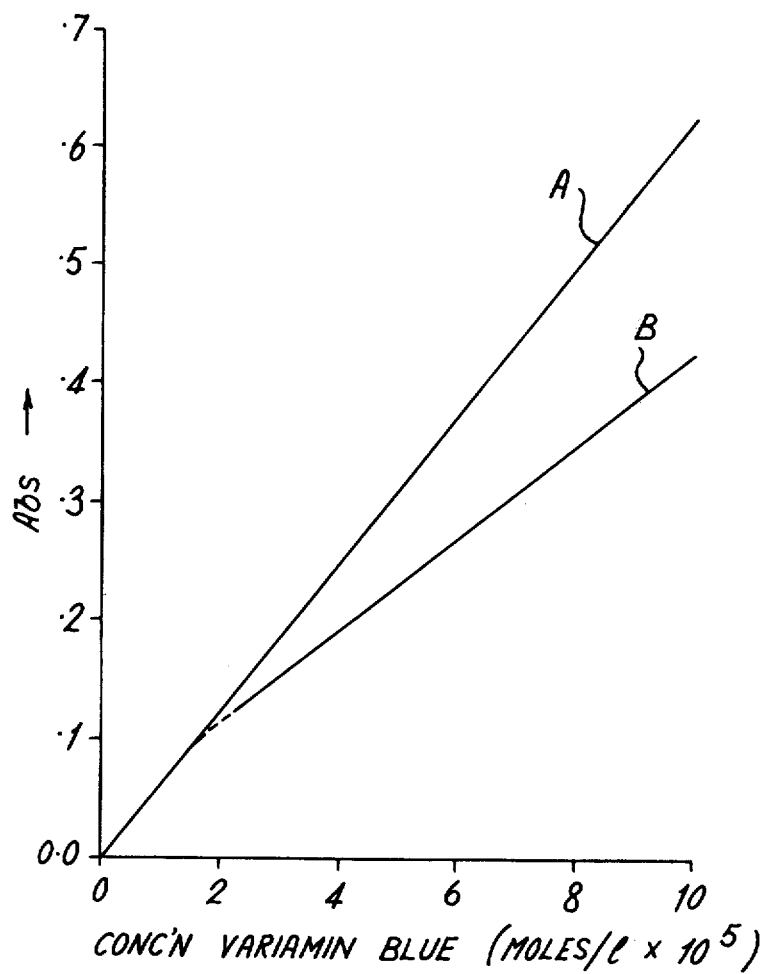

Thus FIGS. 6a and 6b show the results which were obtained from a study of the organic compound Variamin Blue using the apparatus shown in FIGS. 1 to 3, in all cases with a voltage magnitude of two volts. This compound is a member of the redox indicator group and exhibits on oxidation or reduction a change of absorbance in the visible part of the spectrum.

A dilute solution of this compound of approximately $5 \times 10^{-5}$M in an inert background electrolyte of 0.03M potassium sulphate gave a variation of absorbance with wavelength as shown in curve A of FIG. 6a, with the electrode 13 functioning as a cathode. Variamin Blue, as with most redox indicators, is colourless in the reduced form and coloured in the oxidised form so that by inverting the polarities of the electrodes 12 and 13 oxidation was also studied at the surface of electrode 13. Curve B of FIG. 6a shows the variation of absorbance with wavelength of the same solution of Variamin Blue under these conditions.

The graphs of FIG. 6b show how the absorbances of oxidised and reduced Variamin Blue vary at fixed wavelengths with the concentration of the sample (expressed in moles/liter $\times 10^{-5}$). Thus curve A of FIG. 6b shows the variation in absorbance with concentration for oxidation at both 350 and 550 nm. Only a single line is required as the curves obtained were virtually coincident. Curve B of FIG. 6b shows the corresponding curve for reduction at 245 nm.

Similar results have been obtained for the organic compound phenosafranine.

In addition to the analysis of elements and compounds, either organic or inorganic, by the absorption methods described hereinbefore, fluorescence methods may also be used and the general layout of a suitable apparatus for use in such cases is shown in FIG. 4. The apparatus shown in FIG. 4 is similar in many ways to that shown in FIGS. 1 to 3 so that components common to both embodiments have been given the same references. In the embodiment of FIG. 4 the lamp 2 is a xenon arc lamp capable of giving a sufficiently intense beam to excite fluorescence. The plate-like electrode 12 shown in FIG. 3 is replaced by a platinum wire 40 whilst the electrode 13 remains substantially unchanged. The electrodes 40 and 13 are arranged to extend vertically within the cell 3, although again there is grazing incidence as previously defined between the beam and the electrode 13. The lowermost tip of the wire electrode 40 is spaced a short way above the horizontal plane containing the uppermost edge of the electrode 13. Finally the monochromator 5 is positioned at right angles to the optical axis of the light beam so as not to receive light direct from the lamp 2. It will be appreciated that the apparatus will normally include additional optical components similar to those shown in FIG. 1 (e.g. the lenses 6, 7 and 10), but for the sake of simplicity these are not shown in FIG. 4. With this apparatus the occurrence of fluorescence has been detected with sample solutions containing metals such as cadmium and lead.

I claim:

1. A method of analysing material by spectrometry, comprising the steps of:

provided in electrical contact with a pair of charged electrodes an electrolytic medium containing said material in solution to produce a lightabsorbing species in solution by electrolysis at a surface of one of said electrodes, directing through said medium over said surface in a rectilinear path a beam of light having a wavelength for causing said beam to interact with said lightabsorbing species along said path; and detecting the intensity of light emerging from said path.

2. A method according to claim 1, in which said solution contains an inert electrolyte.

3. A method according to claim 1, wherein said providing step includes charging said electrodes with a voltage having a magnitude in the range of about 1 to 2 volts.

4. A method according to claim 1 including the step of providing said beam of light as a single collimated light beam.

5. A method according to claim 1 wherein said light beam directing step includes grazing said surface of said one electrode.

6. A method according to claim 1 wherein said material to be analysed is metallic, and said method includes the steps of making said metallic material at least part of the one of said electrodes which is the anode and anodically stripping material therefrom into said solution.

7. A method according to claim 1 wherein said providing step includes dissolving said material which is to be analysed and then adding the dissolved material to a quantity of an electrolyte solution to form said electrolytic medium.

8. A method according to claim 1 wherein said providing step includes disposing said pair of electrodes in said solution with at least the said surface of said one electrode being rectilinear and said light beam is directed in its said rectilinear path substantially parallel to the interface of said solution and said one rectilinear electrode surface for grazing the latter along the rectilinear distance thereof.

9. A method as in claim 1 wherein said material which is to be analysed is metallic and said one electrode is caused to be a cathode.

10. A method according to claim 1 wherein said emerging light detecting occurs at a point in line with said rectilinear path after said light beam has passed through said medium.

11. A method according to claim 1 including producing fluorescence in said medium by said beam of light, and wherein said light detecting step includes detecting light emerging from said medium perpendicularly of said path.

12. An apparatus for use in analysing material by spectrometry, comprising:

electrolytic cell means including a pair of electrodes for producing electrolysis;

means for directing a beam of light with a given wavelength through said cell in a rectilinear path at grazing incidence to a surface of at least one of said electrodes to cause interaction between said beam and the light-absorbing species developed during said electrolysis when said material is in an electrolytic medium; and means for detecting the intensity of light emerging from said path.

13. An apparatus according to claim 12, further comprising means for maintaining between said electrodes a voltage having a magnitude in the range of about 1 to 2 volts.

14. Apparatus according to claim 12 wherein said detecting means is disposed at a right angle to said path, and further including means for causing said light beam to produce fluorescence in said cell for detection by said detecting means at right angles to said path.

15. Apparatus as in claim 14 wherein said fluorescence causing means includes an xenon arc lamp.

16. Apparatus as in claim 14 wherein the said one electrode is a flat platinum plate, and the other of said electrodes is a platinum wire linearly extending parallel to said flat plate and perpendicularly to said rectilinear light beam path.

17. Apparatus as in claim 12 wherein said pair of electrodes are substantially parallel with a spacing in the order of 5 millimeters, and said light beam is collimated in the order of 0.5 millimeters in diameter with its axis being not further than 1 millimeter from said one electrode surface.

18. Apparatus as in claim 17 wherein said parallel electrodes are both made of platinum.

19. Apparatus as in claim 12 wherein said detecting means is disposed outside of said cell at a position to receive light emerging perpendicularly from said path.

20. Apparatus as in claim 12 wherein said beam of light is a single collimated light beam.

21. Apparatus as in claim 12 wherein said one electrode is parallel to said light beam.

22. Apparatus as in claim 12 wherein the material to be analysed is at least part of one of said electrodes.

23. Apparatus as in claim 12 including an electrolyte solution in said cell means with the said material, which is to be analysed, dissolved in said solution.

24. Apparatus as in claim 12 wherein said detecting means is disposed outside of said cell to receive light emerging therefrom in line with said path.

25. Apparatus as in claim 12 including means for removing electrolyte solution from the cell.

26. Apparatus according to claim 12 including means for deaerating electrolyte solution in said cell.

27. Apparatus for use in analysing material by spectrometry, comprising:

electrolytic cell means containing a pair of electrodes adapted to be charged for providing in electrical contact with said electrodes an electrolytic medium containing said material in solution to produce a light-absorbing species in solution by electrolysis at a surface of one of said electrodes, means for directing through said medium over said surface in a rectilinear path a beam of light having a wavelength for causing said beam to interact with said light-absorbing species along said path, and means for detecting the intensity of light emerging from said path.

* * * * *